United States Patent [19]

Cole et al.

[11] Patent Number: 5,013,317
[45] Date of Patent: May 7, 1991

[54] MEDICAL DRILL ASSEMBLY TRANSPARENT TO X-RAYS AND TARGETING DRILL BIT

[75] Inventors: J. Dean Cole, Orlando, Fla.; A. Glenn Durham, Memphis, Tenn.

[73] Assignee: Smith & Nephew Richards Inc., Memphis, Tenn.

[21] Appl. No.: 476,173

[22] Filed: Feb. 7, 1990

[51] Int. Cl.[5] .................. A61F 5/04; G01C 15/00; A61B 6/08
[52] U.S. Cl. .................................. 606/96; 606/97; 33/286; 378/205
[58] Field of Search .............. 606/96, 97, 98, 80; 33/286, 262, 263, 334; 378/162, 163, 205; 446/144, 145

[56] References Cited

U.S. PATENT DOCUMENTS

| | | | |
|---|---|---|---|
| 371,294 | 10/1887 | Woods | 33/334 |
| 2,502,171 | 3/1950 | Pashby | 33/334 |
| 2,627,698 | 2/1953 | Wood | 446/145 |
| 2,790,084 | 4/1957 | O'Dell | 378/163 |
| 3,011,287 | 12/1961 | Goldfarb | 446/145 |
| 3,859,749 | 1/1975 | Morin | 446/145 |
| 4,222,175 | 9/1980 | Bernicky | 33/263 |
| 4,418,422 | 11/1983 | Richter | 378/205 |
| 4,722,336 | 2/1988 | Kim | 378/162 |
| 4,750,487 | 6/1988 | Zanetti | 378/162 |
| 4,803,976 | 2/1989 | Frigg | 606/97 |
| 4,831,645 | 5/1989 | Guenther | 378/205 |

FOREIGN PATENT DOCUMENTS

| | | |
|---|---|---|
| 0281763 | 9/1988 | European Pat. Off. |
| U18417428 | 9/1984 | Fed. Rep. of Germany |
| CH-A5635998 | 5/1983 | Switzerland |

OTHER PUBLICATIONS

General Electric Brochure: "ULTEM Resin. A Medical Breakthrough. Advanced Technology for Today's Sterilization Techniques", 1984.
General Electric Brochure: "Ultem Resin Design Guide", by G. E. Plastics.

Primary Examiner—Robert A. Hafer
Assistant Examiner—Michael Brown
Attorney, Agent, or Firm—Pravel, Gambrell, Hewitt, Kimball & Krieger

[57] ABSTRACT

A medical drill or pin adapter which is X-ray transparent for aligning a drill bit or pin with an internal line of sight during a surgical procedure utilizes gears mounted within a housing. A drive source engages with the drill adapter rod which in turn rotates, via the gears, a drill bit or pin which is held by the adapter. The drive source is located and oriented out of a line of sight of the direction of the drill bit or pin. The housing, gears and the bit holder for holding the drill bit or pin are formed of X-ray transparent material.

The medical drill or pin adapter can be used in a medical X-ray system for aligning a drill bit or pin with an internal line of sight during a surgical procedure. The system includes an X-ray generating source for creating an X-ray field and an imaging monitor for observing an internal configuration in a patient's body within the X-ray field. A power source for rotating the drill bit is connected to the drill adapter rod and a drill bit is mounted to the drill adapter out of the line of sight of the power source. The drill adapter, formed substantially of X-ray transparent material, operatively connects the power source to the drill bit. The adapter is shaped and dimensioned so that the power source is out of the line of sight of the drill bit when a surgeon is aligning the drill bit in a predetermined direction toward the internal configuration in the X-ray field.

19 Claims, 3 Drawing Sheets

MEDICAL DRILL ASSEMBLY TRANSPARENT TO X-RAYS AND TARGETING DRILL BIT

BACKGROUND OF THE INVENTION

1. Field of the Invention

The present invention relates to medical, operating room power drills which are typically used in conjunction with X-ray machines for drilling precisely-located holes in bone for receiving and anchoring prosthetic implants. More particularly, the invention relates to a radiolucent, e.g. X-ray transparent, drill assembly and targeting drill bit for allowing the holes to be drilled more precisely.

2. Description of the Related Art

Certain surgical procedures require that a surgeon drill and/or place wires, pins or screws (or some other component) through bones or implants which cannot be completely seen without the use of X-ray equipment. For example, when an intramedullary nail is inserted in the medullary canal of a bone, it may be necessary to lock the end of the nail in place by inserting retaining pins, also called transfixion screws or transverse locking screws, through interlocking holes at the distal end of the nail. It is important in the interlocking of intramedullary nails that the orthopedic surgeon know the precise position of the interlocking holes in the nail when drilling through a bone to avoid unnecessary damage to the bone or the nail.

There are several methods currently being used by orthopedic surgeons when drilling through a bone to anchor an intramedullary nail. The methods have been called the "free-hand" method and the distal aiming device method.

In the free-hand method, the surgeon uses a sharp awl, or drill bit, to locate the starting point under X-ray imaging. The surgeon then rotates the drill point parallel to the line of X-ray and forces the sharp pointed instrument through the bone and through the intramedullary nail. This method, although quick and relatively accurate for surgeons who frequently use it, can increase the amount of radiation the surgeon receives because his or her hand must remain in the path of the X-rays for a period of time.

In the distal aiming device method, a distal aiming device, such as an X-ray transparent target, is used to assist in locating the correct path of transfixion screws for anchoring the intramedullary nail so that the drill bit goes through the hole in the nail and opens a path in the bone for the locking screw. There are distal aiming devices in which a drill template is adjusted and ultimately fixed in the desired position by means of an X-ray image amplifier. For example, Swiss Pat. No. CH-A5 635 998 discloses an aiming device which has an aiming head with a hole for the insertion of a directional socket. The aiming head mounting is positioned in a holder that is connected to the X-ray machine and is suspended from the X-ray machine. This arrangement makes it difficult to position the apparatus and to fix it in position, with resulting unsatisfactory target precision. In addition, the stationary arrangement limits operation.

There is an aiming device that can be used independently of an X-ray machine, described in German industrial design patent U1 84 17 428. A device with a receiving head rests in a holder and is permeable to X-rays, and which accepts a drill bit or a drill wire. Even this improved device, however, has major disadvantages. In particular, the aiming process takes place during the drilling of the bone, which causes considerable darkening of the working field and low image resolution.

U.S. Pat. No. 4,803,976 describes another aiming device which may be held between a radiation source and a radiation receiver, the position of which can be represented visibly by means of an image converter, allowing continuous adjustment of its orientation. The device has a socket for the drill bit and a direction finder which must be maintained in a defined position relative to one another during the drilling process. This device still has the disadvantage that it does not permit direct observation of the drill bit as it drills through the bone and nail because of the obstruction in the radiation field resulting from the power drill which is in the same line of sight as the drill bit.

SUMMARY OF THE INVENTION

The present invention overcomes the drawbacks of the prior art devices and methods described above by providing a device which allows the surgeon to observe the drill bit on a monitor of an X-ray image converter as the bit drills through the bone and intramedullary nail opening.

The invention includes a radiolucent offset drill assembly with a drive mechanism for transmitting rotational energy from a drill to a drill bit where the drill is out of the line of sight of the axis of the drill bit so that only the drill bit can be seen on a standard X-ray image monitor. The drill bit is formed with a metal bit portion mounted in a holder formed of an X-ray transparent material so that the bit can be targeted through the use of an X-ray image monitor.

In a preferred embodiment, the assembly includes a gear box housing which contains two shafts connected to each other through appropriate gears or the like. One of the shafts is connected to a drive source such as a power drill. The other shaft extends through the gear box housing and is adapted to receive a drill bit. As the one shaft is rotated by the power drill, the other shaft through the gears causes the drill bit to rotate.

The entire offset drill assembly is formed of X-ray transparent or radiolucent materials with the exception of the drill bit and an adapter for connecting the one shaft to the power source. The gears allow the drill bit to be offset from the power source, preferably by 90°, so the plane of the drill bit is perpendicular to the plane of the power drill or other power source. The drill bit is formed so that only the bit and not the bit holder shows up on the X-ray image monitor. In this way the power drill and other non-X-ray transparent parts are removed from the radiation field and the precise orientation of the drill bit can be observed on the monitor of the X-ray image converter as the drill bit drills through the bone to the target interlocking hole in, for example, an intramedullary nail.

BRIEF DESCRIPTION OF THE DRAWINGS

A better understanding of the invention can be obtained when the following detailed description of an exemplary embodiment of the invention is considered in conjunction with the accompanying drawings, in which.

DETAILED DESCRIPTION OF AN EXEMPLARY EMBODIMENT

Figure 1:
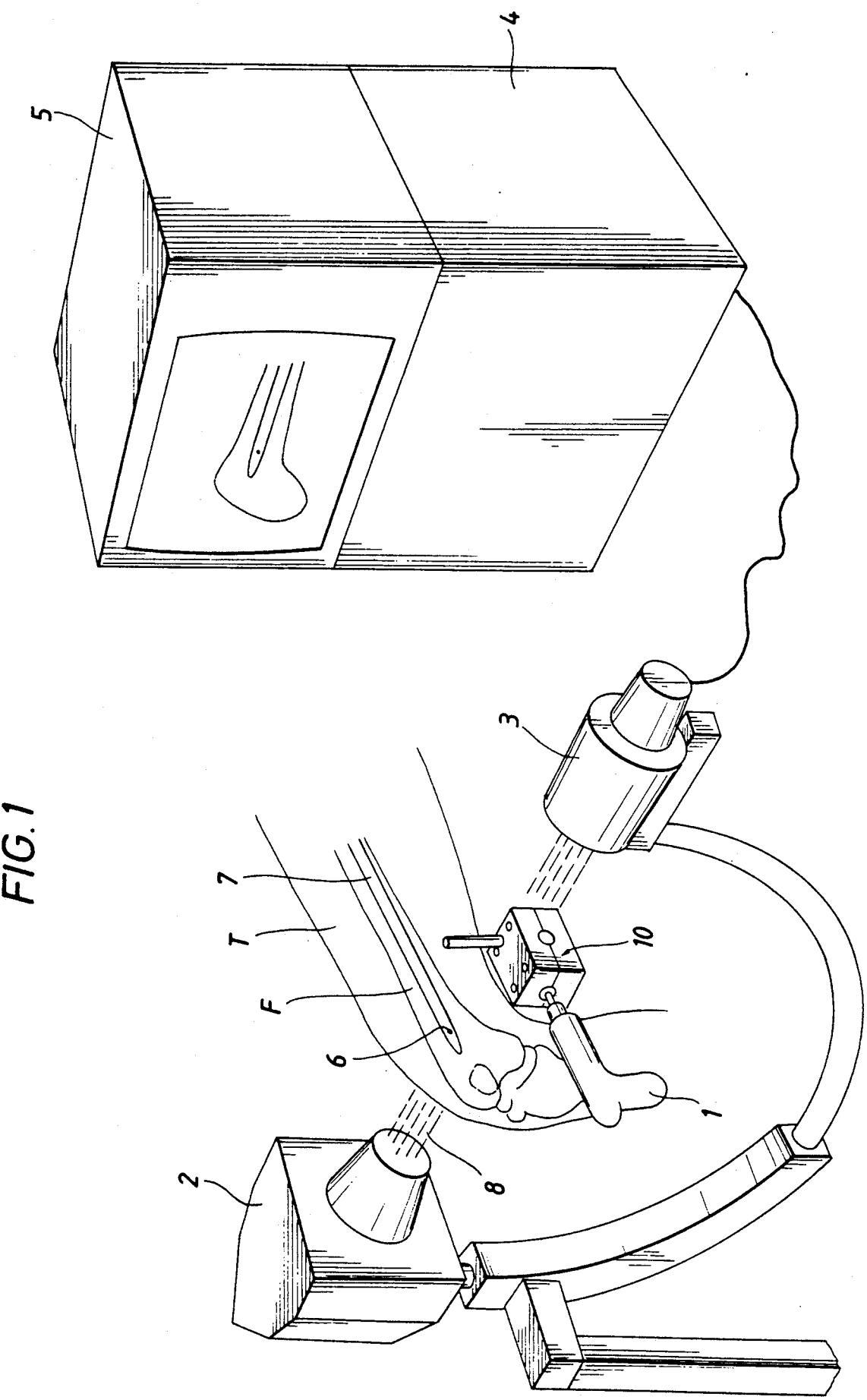
FIG. 1 is a perspective view of the radiolucent offset drill assembly of the subject invention and a power drill and associated X-ray equipment.

An exemplary embodiment of a radiolucent offset drill assembly which is the subject of the invention is shown in FIG. 1 and designated generally by reference numeral 10. The drill assembly 10 is driven by a power drill 1, in this case a standard medical operating room power drill, for rotating a drill bit 12. The drill assembly 10 is used in conjunction with an X-ray source 2, an X-ray receiver 3, and an image converter 4 having a monitor 5 connected to the X-ray receiver 3.

In a radiation field 8 generated by the X-ray source 2 and receiver 3, a patient's thigh T is shown positioned with an intramedullary nail 7 inserted in the medulla of a femur F. The orientation of the drill bit 12 with regard to an interlocking hole 6 in the intramedullary nail 7 can be observed on the monitor 5 of the image converter 4 because the drill assembly 10 and all of its component parts described below are transparent to X-rays and the drill 1 is not in the path of the X-rays.

Figure 2:
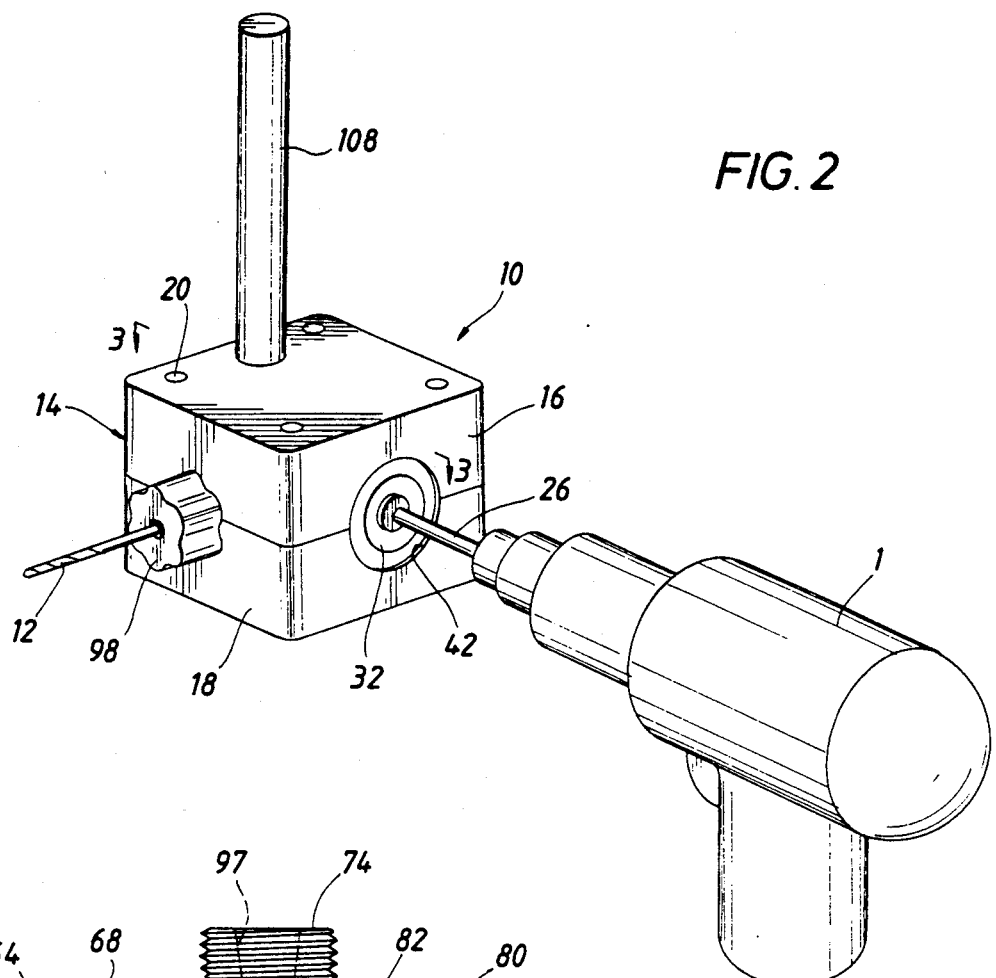
FIG. 2 is a perspective view of the drill assembly of FIG. 1, rotated 90° to show the drill bit relative to the drill.
Figure 3:
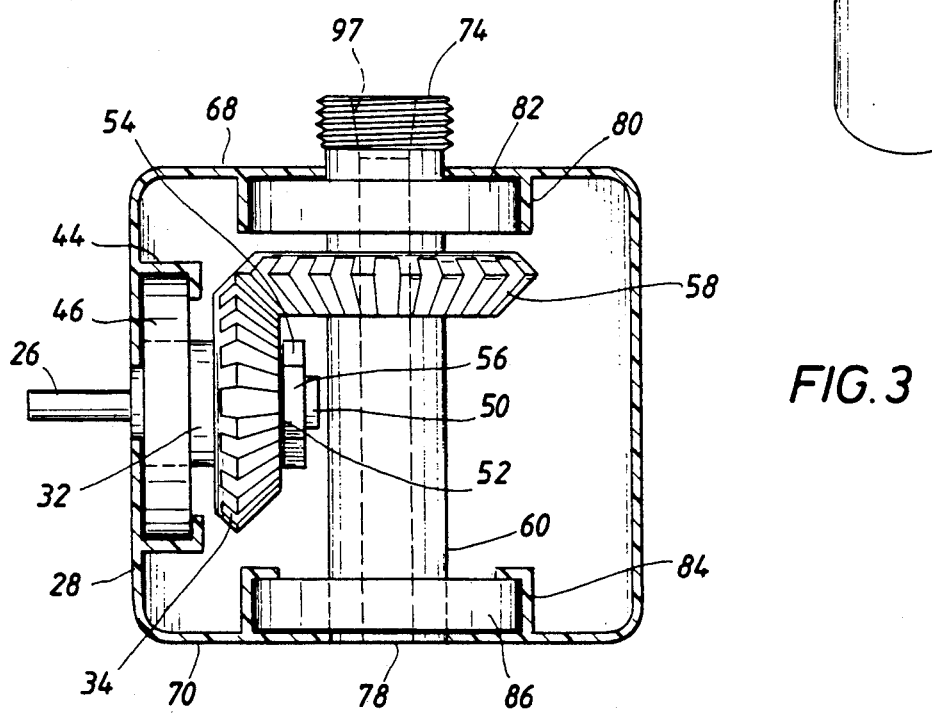
FIG. 3 is a sectional view looking along section lines 3—3 of FIG. 2.
Figure 4:
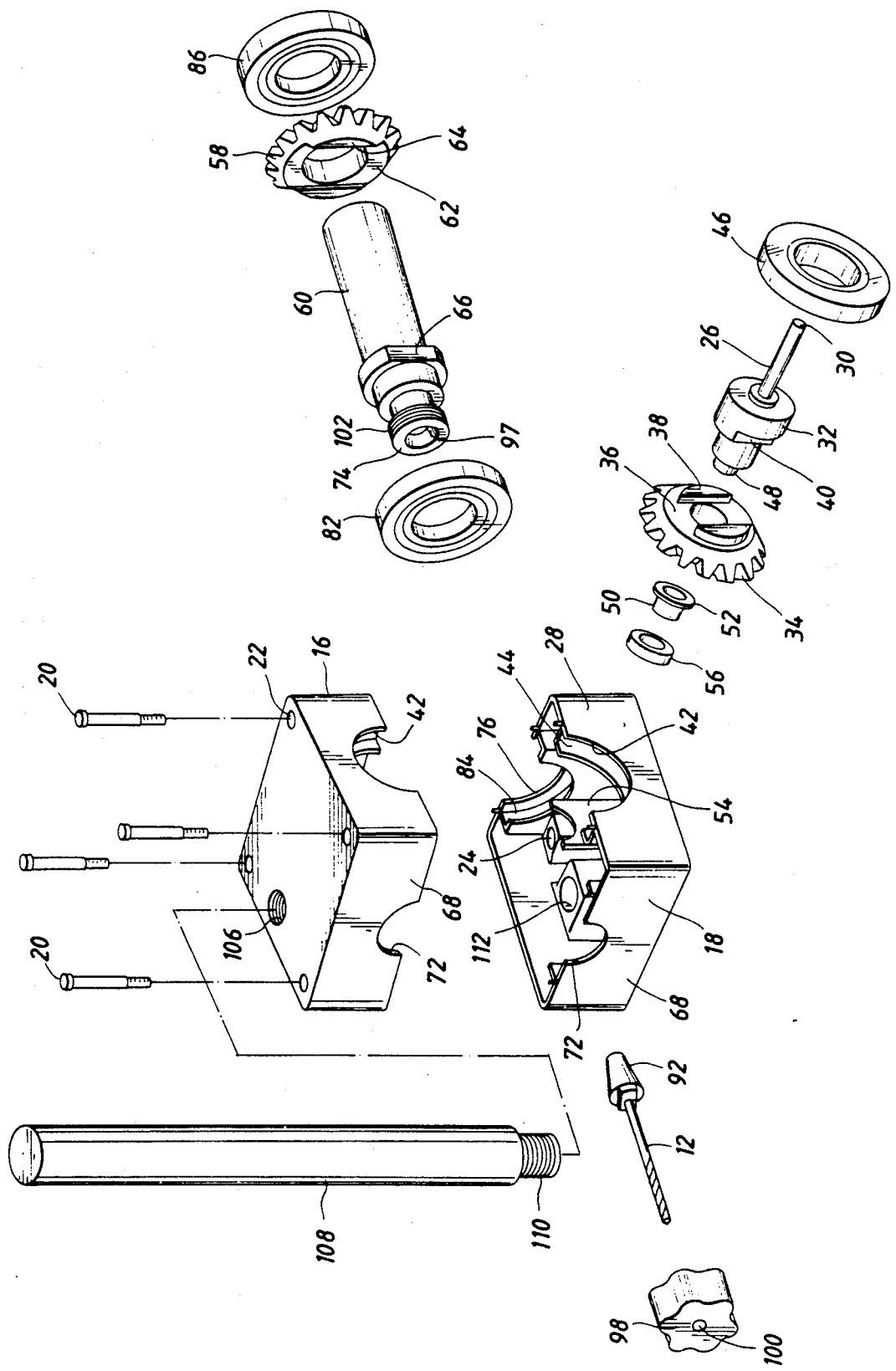
FIG. 4 is an exploded view of the drill assembly of FIGS. 2 and 3.

Referring to FIGS. 2, 3, and 4, the drill assembly 10 includes a gear box housing 14 with two halves, an upper half 16 and a lower half 18. The gear box housing 14 is made out of a material that is transparent to X-rays and is autoclavable so that the drill assembly can be sterilized and reused and at the same time be strong enough to perform as described. Such a material is a polyetherimide known as ULTEM ®, which is a thermoplastic material sold by General Electric Company.

The two halves 16, 18 are held together with bolts 20 which are inserted through apertures 22 in the upper half 16. The bolts 20 engage internally threaded apertures 24 in the lower half 18 of the gear box housing 14. The bolts 20 are made out of a nylon or other X-ray transparent material.

The drill assembly 10 is driven by a standard operating room power drill 1 shown in FIGS. 1 and 2. Preferably, the drill 1 is offset 90° from the drill bit 12 as best shown in FIGS. 1 and 2. Other angles may be used.

Instead of a gear assembly as described, the offset drill assembly can be formed of a flexible shaft (not shown), universal connection (not shown) or other assembly for allowing a standard drill to drive a drill bit 12 and at the same time be out of the line of site along the axis of the drill bit 12. One of the important characteristics of the invention is to remove the drill from the path of the X-rays so that the orientation and location of the drill bit can be observed at all times by the operating physician.

The power drill 1 engages an adapter rod 26 which extends from one face 28 of the gear box housing 14. The adapter rod 26 is generally irregular in cross-section, preferably triangular, to provide a firm engagement with the power drill 1. The adapter rod 26 is preferably formed of metal because of the strength requirements for engagement with the power drill 1.

The adapter rod 26 is connected to a drive shaft 32 which is made out of the ULTEM ® resin material mentioned above. A bevel gear 34 formed of DELRIN ® or other X-ray transparent material, is mounted on the drive shaft 32. A rear face 36 of the gear 34 has a pair of raised surfaces 38 which abut a pair of cooperating notched surfaces 40 of the drive shaft 32 which prevent rotational slippage of the gear 34 on the drive shaft 32. A drive shaft aperture 42 is formed in the face 28 of the housing 14. A bearing race 44 is located immediately behind the aperture 42 to receive a bearing 46 which fits onto the drive shaft 32 and includes plastic ball bearings formed of a suitable resin such as DELRIN ®, a thermoplastic material of DuPont, Inc. The inner end 48 of the drive shaft 32 extends beyond the gear 34 and a bushing 50 with a flange 52 is inserted over the inner end 48. A larger bushing 56 is inserted over the bushing 50 and is positioned between mating half saddle supports 54 which are formed in the halves 16, 18 of the gear box housing 14. The small and large bushings 50 and 56 can be formed of teflon or other suitable radiolucent material.

The gear 34 meshes with a bevel gear 58 formed of DELRIN ® which is mounted on a drill bit drive shaft 60 formed of ULTEM ® plastic. The drill shaft gear 58 has a rear face 62 with a pair of raised surfaces 64 engage corresponding receiving surfaces 66 of the drill shaft 60 to lock the gear 58 to the drill shaft 60.

The drill shaft 60 is oriented perpendicular to the drive shaft 32 and extends through the front face 68 of the gear box housing 14. The front face 68 has a front aperture 72 through which a drill bit receiving end 74 of the drill drive shaft 60 extends. The rear face 70 has a rear aperture 76 for exposing a hollow rear end 78 of the drill drive shaft member 60. A bearing race 80 is formed immediately behind the front aperture 72 to receive a bearing 82 which fits onto the drill shaft 60. A rear drill shaft bearing race 84 is formed immediately adjacent to the rear aperture 76 to receive a bearing 86 which fits onto the drill shaft member 60. The bearings 82, 86 include plastic ball bearings (not shown) formed of DELRIN ®.

Figure 5:
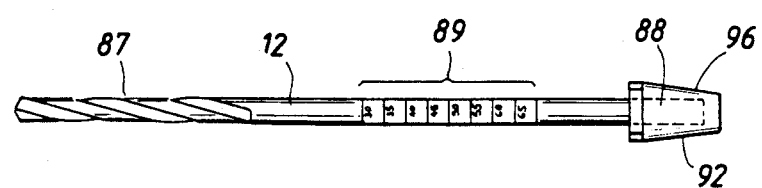
FIG. 5 is an enlarged plan view of a drill bit shown in FIG. 4.

The drill bit 12 is a standard operating room drill bit formed of stainless steel. One end of the drill bit 12 has flutes 87 formed on it while the other end is a drill shank 88 that is fixed to a bit holder 92 with a tapered outer surface 96, as shown in FIG. 5, formed of an X-ray transparent material such as a suitable high strength plastic as an acetal copolymer. The bit holder 92 can be molded or mounted through an adhesive to the shank 88 which is irregular in shape to resist rotation of the holder 92 relative to the shank 88. By forming the holder 88 of an X-ray transparent material a more precise targeting can be achieved because only the drill bit will show up on the X-ray image monitor. A series of numbered depth indicators generally designated by reference numeral 89 are formed on the outer surface of the drill bit 12 to indicate to the surgeon the depth of the drilled hole.

A cooperating, tapered receiving opening 97 is formed in the drill bit receiving end 74 of the drill drive shaft 60 (FIG. 4). After the bit holder 92 is inserted in the drill bit receiving end 74 of the drill drive shaft 60, a locking knob 98 having a central aperture 100 and internal threads (not shown) is placed over the drill bit 12 so that the drill shank 88 extends through the central aperture 100 of the locking knob 98. The locking knob 98 is threaded onto the external threads 102 on the drill bit receiving end 74 of the drill drive shaft 60. The locking knob 98 holds the bit holder 92 against the receiving opening 97 to eliminate any slippage between the two surfaces. The bit holder 92 can also be modified to accept other types of instruments or tools requiring a rotational torque as, for example, locking screws, bolts or guidewires for spiral pedicle screws, sacral screw fixation, pelvic screw-fixation, or any other surgery requiring precisely-placed guidewires or screws.

The upper half 16 of the gear box housing 14 has a recessed threaded aperture 106 for receiving a handle 108 having a threaded end 110. A similar recessed threaded aperture 112 can also be provided in the lower half 18 of the gear box housing 14 to provide the operator with maximum versatility in the use of the offset drill assembly 10.

In use, the surgeon holds the power drill 1 in one hand and the handle 108 in the other hand, with the offset drill assembly 10 positioned in the radiation field 8 and the drill 1 outside the radiation field (FIG. 1). The drill bit 12 is aligned, for example, with the interlocking hole 6 in the intramedullary nail 7 by the surgeon viewing the image monitor 5. Once properly aligned, the bone is drilled. Continuous observation on the monitor 5 during the drilling process permits the surgeon to accurately and precisely align the targeted interlocking hole 6 with the corresponding opening in the intramedullary nail 7.

The radiolucent offset drill assembly 10 permits high image resolution on the monitor 5. The high image resolution results not only from the fact that the drill assembly 10 is made primarily of radiolucent materials and the nearest metal around the drill bit 12 is approximately 1½" away (the adapter rod 26), but also due to the fact that the drill bit drive shaft member 60 is substantially hollow with the exception of the conically shaped receiving area 97 of the drill bit drive shaft member 60. Thus, minimal darkening occurs within the immediate area surrounding the targeted interlocking hole 6. Additionally, the offset drill assembly 10 reduces the amount of radiation that the surgeon would receive since the surgeon's hands are outside the radiation field 8.

It is intended that the foregoing description of the exemplary embodiment of the invention is not to be limiting but improvements and modifications can be made without departure from the spirit and scope of the invention, which is defined in the appended claims.

We claim:

1. An X-ray transparent adapter for aligning a drill bit, pin or other elongated member, the adapter being capable of connecting to a drive source, comprising:
   a drive means having a first end and a second end;
   means for holding the elongated member connected to said first end of said drive means;
   means for engaging the drive source connected to said second end of said drive means;
   said drive means being adapted to rotate the elongated member when driven by the drive source;
   at least said drive means and said means for holding the elongated member being formed of X-ray transparent material so that an operator can align the elongated member with an internal predetermined direction in an X-ray transparent medium; and
   said means for holding and said means for engaging being located and oriented relative to each other so that the drive source is out of the X-ray line of sight when the operator aligns the elongated member with the internal predetermined direction.

2. The adapter of claim 1, wherein said adapter is autoclavable.

3. The adapter of claim 1, wherein said means for engaging the drive source comprises an irregularly-shaped metal rod adapted to be engaged by a power drill.

4. The adapter of claim 1, wherein said drive means comprises gear means formed of a thermoplastic material.

5. The adapter of claim 4, wherein the gear means comprises:
   a pair of drive shafts respectively connected to said means for holding and said means for engaging; and
   a pair of cooperating bevel gears respectively mounted on said drive shafts.

6. The adapter of claim 5, wherein said drive shafts are oriented ninety degrees relative to each other.

7. The adapter of claim 1, further comprising:
   a housing formed in two halves, said housing encases said drive means; and
   a plurality of bolts formed of an X-ray transparent material for connecting the two halves.

8. The adapter of claim 7, wherein said housing is formed of a polyetherimide thermoplastic material.

9. The adapter of claim 7, further comprising a handle connected to said housing.

10. An X-ray system for aligning a drill bit, pin or other elongated member with an internal line of sight during a surgical procedure, comprising:
    an X-ray generating means for generating a radiation field;
    a receiving means for receiving the radiation field;
    an imaging means for observing an internal configuration in a patient's body within the radiation field, said imaging means being electrically connected to said receiving means;
    an elongated member for drilling a hole or inserting a pin within the internal configuration;
    a drive source for rotating said elongated member; and
    an adapter substantially formed of an X-ray transparent material for operatively connecting said drive source to said elongated member, said adapter being shaped and dimensioned so that said drive source is not in the X-ray line of sight of the radiation field permitting a surgeon to observe on said imaging means the alignment of said elongated member in a predetermined direction toward the internal configuration in the patient's body with the radiation field.

11. The system of claim 10, wherein said adapter comprises:
    a housing;
    a drive means having a first end and a second end;
    means for holding said elongated member connected to said first end of said drive means; and
    means for engaging said drive source connected to said second end of said drive means.

12. The system of claim 11, wherein said housing is formed of a polyetherimide thermoplastic material.

13. The system of claim 11, wherein said housing is formed in two halves which are held together by a plurality of bolts formed of an X-ray transparent material.

14. The system of claim 11, wherein said drive means comprises gear means formed of a thermoplastic material.

15. The system of claim 14, wherein said gear means comprises:
- a pair of drive shafts respectively connected to said means for holding and said means for engaging; and
- a pair of cooperating bevel gears respectively mounted on said drive shafts.

16. The system of claim 15, wherein said drive shafts are oriented ninety degrees relative to each other.

17. The system of claim 11, further comprising a handle connected to said housing.

18. The system of claim 10, wherein said adapter is autoclavable.

19. A method of aligning a drill bit, pin or other elongated member in an internal predetermined direction of a target in an x-ray transparent medium, comprising the steps of:

placing said target in a radiation field between a x-ray generating means and a x-ray receiving means;

aligning the internal predetermined direction of the target and x-rays in said radiation field by viewing said target on an imaging means electrically connected to said x-ray receiving means;

positioning an adapter with said elongated member in said radiation field;

aligning said elongated member with said internal predetermined direction of said target by viewing on said imaging means;

rotating said elongated member with a drive source connected to said adapter;

observing the alignment of said elongated member with said internal predetermined direction of said target as said elongated member advances toward said target.

* * * * *